United States Patent [19]

Ardis et al.

[11] 4,009,182
[45] Feb. 22, 1977

[54] PROCESS FOR PREPARING 3-HYDROXYOXETANE

[75] Inventors: Alan E. Ardis, North Haven; John A. Wojtowicz, East Haven, both of Conn.

[73] Assignee: Olin Corporation, New Haven, Conn.

[22] Filed: Aug. 22, 1968

[21] Appl. No.: 798,473

Related U.S. Application Data

[62] Division of Ser. No. 557,377, June 14, 1966, Pat. No. 3,446,819.

[52] U.S. Cl. .............................................. 260/333
[51] Int. Cl.$^2$ ...................................... C07D 305/08
[58] Field of Search ............ 260/632 B, 333, 601 H

[56] References Cited

UNITED STATES PATENTS

| 2,533,172 | 12/1950 | McKinley ..................... 260/632 X |
| 2,662,919 | 12/1953 | Hagemeyer et al. ........... 260/632 X |

| 3,449,369 | 6/1969 | Berezin ........................... 260/333 |

OTHER PUBLICATIONS

Houben–Weyl, Methoden der Organischen Chemie, vol. VI/3 (1965) p. 153.

*Primary Examiner*—Norma S. Milestone
*Attorney, Agent, or Firm*—F. A. Iskander; T. P. O'Day

[57] ABSTRACT

Hydroxyoxetanes of the formula

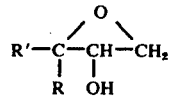

wherein R and R' are each selected from the group consisting of hydrogen and alkyl of from 1 to 5 carbon atoms.

1 Claim, No Drawings

PROCESS FOR PREPARING 3-HYDROXYOXETANE

This application is a division of co-pending application Ser. No. 557,377, filed June 14, 1966, now U.S. Pat. No. 3,446,819, by Alan E. Ardis and John A. Wojtowicz.

This invention relates to the preparation of novel alkenoxyoxetanes. More particularly, this invention relates to novel alkenoxyoxetanes and to a process for their preparation in which an allyloxyoxetane compound is isomerized to the corresponding alkenoxyoxetane compound in the presence of a catalyst. In another aspect, this invention relates to the preparation of hydroxy oxetanes by the hypochlorination of an alkenoxyoxetane compound.

The novel alkenoxyoxetanes of this invention have the formula:

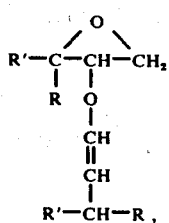

wherein R and R' are each selected from the group consisting of hydrogen and alkyl of from 1 to 5 inclusive carbon atoms.

Hydroxyoxetanes of this invention have the formula:

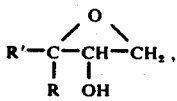

wherein R and R' are each selected from the group consisting of hydrogen and alkyl of from 1 to 5 inclusive carbon atoms.

Preparation of Alkenoxyoxetanes

In preparing the novel alkenoxyoxetanes of this invention an allyloxyoxetane compound of the formula:

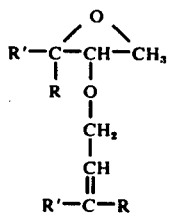

wherein R and R' are each selected from the group consisting of hydrogen and alkyl of from 1 to 5 inclusive carbon atoms, is isomerized in the presence of a suitable catalyst at a temperature of from about 0° to about 100° C. to yield the corresponding alkenoxyoxetane.

Allyloxyoxetane compounds useful in preparing the novel alkenoxyoxetane compounds of this invention include 3-allyloxyoxetane, 3(3'-methyl) allyloxyoxetane, 3(3',3'-dimethyl) allyloxyoxetane, 3(3'-methyl-3'-ethyl) allyloxyoxetane, 3(3'-ethyl-3'-propyl) allyloxyoxetane, 3(3',3'-dipropyl) allyloxyoxetane, 3(3'-methyl-3'-isopropyl) allyloxyoxetane, 3(3'-ethyl-3'-isopropyl) allyloxyoxetane, 3(3',3'-dibutyl) allyloxyoxetane, 3',3'-methyl-3'-isobutyl) allyloxyoxetane, 3(3'-ethyl-3'-isobutyl) allyloxyoxetane, 3'(3'-methyl-3'-amyl) allyloxyoxetane, 3(3'-isopropyl-3'-amyl) allyloxyoxetane, 3(3'-butyl-3'-isoamyl) allyloxyoxetane, 3(3',3'-diisoamyl) allyloxyoxetane, etc. Preferably, the isomerization reaction is carried out in the presence of an inert organic solvent. The useful solvents include hexamethylphosphoramide dimethylsulfoxide, 1,2-dimethoxyethane, dimethylformamide, dimethylacetamide, tetrahydrofuran, sulfolane, etc. A wide variety of catalysts can be employed in affecting the isomerization reaction. Suitable basic catalysts include potassium t-butoxide, sodium hydroxide, potassium hydroxide, sodium t-butoxide, lithium t-butoxide, lithium hydroxide, etc.

After filtration of the reaction mixture to remove any insoluble materials which may have formed during the isomerization reaction the alkenoxyoxetane product can be recovered by any of a variety of methods known in the art, such as by distillation, extraction, etc.

The starting allyloxyoxetane compounds can be obtained in the manner described in Polak et al application Ser. No. 399,852, filed September 28, 1964 and now abandoned. For example, allyloxyoxetane, which has the formula:

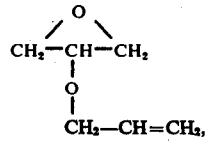

can be prepared by first reacting allyl alcohol with gaseous chlorine at a temperature below 50° C. to yield a reaction mixture containing 2-allyloxy-3-chloro-1-propanol which, in turn, is dehydrohalogenated in the presence of aqueous sodium hydroxide at a temperature below 100°–110° C. to yield allyloxyoxetane.

Preparation of Hydroxyoxetanes

According to the process of this invention hydroxyoxetane compounds can be prepared by hypochlorinating the novel alkenoxyoxetanes of the formula:

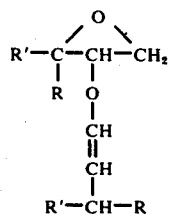

wherein R and R' have the same meaning as previously described. The reaction is conveniently carried out by passing gaseous chlorine into a solution of the alkenoxyoxetane, for example, propenoxyoxetane in a water-acetone or water-dioxane mixture. If desired, the reaction can be conducted by adding liquid chlorine to the alkenoxyoxetane dissolved in a suitable solvent. Usually about 1 mole of chlorine is utilized per mole of the starting alkenoxyoxetane.

Generally the hypochlorination reaction is conducted at a temperature of from about −20° to +50° C. and preferably, at a temperature of from about 0° to +25° C. In order to achieve high yields it is necessary to employ a hydrogen chloride acceptor in the reaction mixture. Useful hydrogen chloride acceptors include calcium carbonate, sodium carbonate, sodium hydroxide, potassium hydroxide, sodium bicarbonate, lime, etc. The stoichiometric requirement of the acid acceptor can be employed although an excess of up to 200 per cent or more may be used, if desired.

Starting alkenoxyoxetanes useful in preparing hydroxyoxetanes by the novel process of this invention include 3-n-propenoxyoxetane, 3-n-butenoxyoxetane, 3-isobutenoxyoxetane, 3-n-amylenoxyoxetane, 3-n-heptenoxyoxetane, etc.

EXAMPLE I

Preparation of Propenoxyoxetane

Allyloxyoxetane (456 g.) and 700 g. of dimethylsulfoxide were placed in a two-liter, three-necked flask and, with stirring, 51 g. of potassium t-butoxide was added at room temperature over a 5–10 minute period. An exothermic reaction occurred with the temperature rising to a maximum of 45°–55° C. after 30 minutes. After allowing the reaction mixture to cool for 30 minutes, examination of the mixture by near infrared indicated complete conversion of the allyloxyoxetane to propenoxyoxetane. The crude reaction product was filtered and the filtrate distilled through a 24 inch Goodloe column. A total of 388 g. of 3-propenoxyoxetane, b.p. 75° C. at 50 mm Hg, $n_D^{25}$ 1.4426, (85 per cent yield) of the formula:

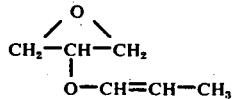

was recovered at 73°–77° C. under 50 mm Hg.

Anal. Calc'd for $C_6H_{10}O_2$: C, 63.0; H, 8.78. Found: C, 62.4 H, 8.89.

EXAMPLE II – III

Two additional experiments were performed in the same manner as described in Example I. Details relating to these two examples are given in the Table below:

| Example | Allyloxyoxetane g. | moles | Dimethylsulfoxide g. | Potassium t-Butoxide g. | Propenoxy Oxetane g. | moles | Yield (Per Cent) |
|---|---|---|---|---|---|---|---|
| II | 864 | 7.6 | 1344 | 100 | 735 | 6.45 | 85 |
| III | 1730 | 15.2 | 2688 | 220 | 1510 | 13.2 | 87.5 |

EXAMPLE IV

Preparation of Hydroxyoxetane

3-Propenoxyoxetane (16.7 g., 0.146 mole) was hypochlorinated in a water (238 g.) - acetone (77.5 g.) mixture at 0° to 10° in the presence of $CaCO_3$ (13.8 g., 0.138 mole) as a hydrogen chloride acceptor. The reactor was a 500 ml. flask equipped with stirrer, chlorine sparger and platinum and calomel electrodes (attached to pH meter) for monitoring the oxidation potential. Chlorine was introduced at a rate of about 6.5 millimoles per minute for 23.5 minutes. Chromatographic analysis showed that the propenoxyoxetane had been completely consumed. Two new peaks were observed; the first alpha-chloropropionaldehyde eluting just after water and, the second being a higher boiling component having a retention time slightly greater than that of glycidol. The latter peak was identified as hydroxyoxetane by infrared and nuclear magnetic resonance studies. After the reaction mixture had been filtered, the filtrate was saturated with sodium chloride and then extracted six times with 200 ml. portions of methyl ethyl ketone and twice with 50 ml. portions of butanol. The combined extracts were dried over anhydrous magnesium sulfate and the solvents removed under atmospheric pressure (max. head temperature 81° C.). Distillation of the concentrated residue under reduced pressure yielded a main fraction of 3-hydroxyoxetane, 6.6 g., at 80° C./10 mm Hg. Chromatographic analysis of all fractions as well as of the flask residue indicated a yield of about 70 per cent of 3-hydroxyoxetane. Redistillation of the main fraction gave pure 3-hydroxyoxetane, a colorless liquid, b.p. 72° C. at 10 mm Hg, $n_D^{25}$ 1.4335, $d_4^{28}$ 1.125, having the formula:

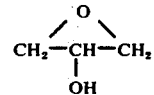

Anal. Calc'd for $C_3H_6O_2$: C, 48.64; H, 8.16. Found: C, 47.8; H, 8.1.

The hydroxyoxetanes of this invention can be reacted with organic phosphites to yield oxetane ring-containing phosphites which are useful as stabilizers for halogen-containing resins. For example, 2 moles of the compound:

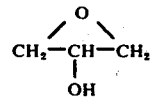

can be reacted with 0.5 mole of triphenyl phosphite by heating the two reactants from about 2 hours at 130°–160° C. (15 mm Hg. pressure) in the presence of about 0.5 gram of sodium methylate to yield tri-oxetyl phosphite of the formula:

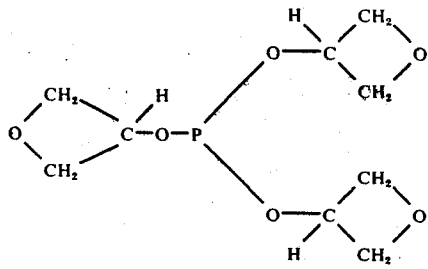

(I)

The phosphite compounds of the type of (I), which are particularly valuable as stabilizers for halogen-containing resins, can be employed in an amount of from about 0.005 to about 15 per cent, preferably from about 0.5 to 6 per cent, by weight of the resin. These phosphite stabilizers are especially useful when employed with halogen-containing vinyl and vinylidene resins in which the halogen is attached directly to the carbon atoms. For example, vinyl chloride resins can be stabilized with materials of this type as also can be resins composed of mixtures of chlorinated polyethylene, polyvinyl chloride, etc. These stabilizers can be incorporated with the resin by milling on rolls at 100° to 150° C. or by any other of the methods well known in the art which provide for uniform distribution of the compound added throughout the resin. Additional details on the use of phosphite stabilizers of this type can be found in Hechenbleikner et al U.S. Pat. No. 3,209,013.

What is claimed is:

1. A process for the preparation of a hydroxyoxetane of the formula:

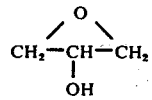

which comprises reacting chlorine with a compound of the formula:

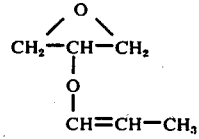

at a temperature of from about −20° to about 50° C in the presence of a water-acetone mixture and in the presence of calcium carbonate.

* * * * *